US011216760B1

(12) United States Patent
Moisan et al.

(10) Patent No.: US 11,216,760 B1
(45) Date of Patent: Jan. 4, 2022

(54) SYSTEM AND METHOD FOR INVENTORY PLANNING IN A SUPPLY CHAIN NETWORK

(71) Applicant: JDA Software Group, Inc., Scottsdale, AZ (US)

(72) Inventors: Thierry Moisan, Montréal (CA); Eric Prescott-Gagnon, Montréal (CA); Yossiri Adulyasak, Montréal (CA)

(73) Assignee: Blue Yonder Group, Inc., Scottsdale, AZ (US)

( * ) Notice: Subject to any disclaimer, the term of this patent is extended or adjusted under 35 U.S.C. 154(b) by 569 days.

(21) Appl. No.: 15/585,594

(22) Filed: May 3, 2017

Related U.S. Application Data (60) Provisional application No. 62/336,244, filed on May 13, 2016.

(51) Int. Cl.
*G06Q 10/06* (2012.01)
*G06Q 10/08* (2012.01)

(52) U.S. Cl.
CPC ..... *G06Q 10/06315* (2013.01); *G06Q 10/087* (2013.01)

(58) Field of Classification Search
CPC .............................. G06Q 10/06315
See application file for complete search history.

(56) References Cited

U.S. PATENT DOCUMENTS

| | | | | | |
|---|---|---|---|---|---|
| 5,946,662 | A | * | 8/1999 | Ettl | G06Q 10/06315 705/7.26 |
| 5,953,707 | A | * | 9/1999 | Huang | G06Q 10/06 705/7.25 |
| 7,092,929 | B1 | * | 8/2006 | Dvorak | G06Q 10/087 705/28 |
| 8,700,443 | B1 | * | 4/2014 | Murray | G06Q 10/087 705/7.31 |
| 2002/0138358 | A1 | * | 9/2002 | Scheer | G06Q 10/063 705/7.36 |
| 2002/0143598 | A1 | * | 10/2002 | Scheer | G06Q 10/06 705/7.26 |
| 2002/0143669 | A1 | * | 10/2002 | Scheer | G06Q 10/087 705/28 |
| 2002/0161674 | A1 | * | 10/2002 | Scheer | G06Q 10/0631 705/28 |

(Continued)

OTHER PUBLICATIONS

Alin Constantin Rádáşanu, Inventory Management, Service Level and Safety Stock, Journal of Public Administration, Finance and Law, Issue Sep. 2016, pp. 145-153 (Year: 2016).*

(Continued)

*Primary Examiner* — Andre D Boyce
(74) *Attorney, Agent, or Firm* — Spencer Fane LLP; Steven J. Laureanti (57) ABSTRACT

A system and method are disclosed for searching alternate inventory policies from an initial inventory policy of an inventory of one or more supply chain entities to a target inventory policy by receiving a current state of items in a supply chain network determining an initial inventory policy comprising a reorder point and a target quantity, identifying one or more provisional inventory policies calculating a cost, a fill rate, and a no-stockout probability, and transporting items among the one or more supply chain entities to restock the inventory.

20 Claims, 4 Drawing Sheets

(56) References Cited

U.S. PATENT DOCUMENTS

| | | | | |
|---|---|---|---|---|
| 2003/0083947 A1* | 5/2003 | Hoffman | ................ | G06Q 10/06 705/22 |
| 2003/0101107 A1* | 5/2003 | Agarwal | ............. | G06Q 10/087 705/28 |
| 2004/0153187 A1* | 8/2004 | Knight | ................... | G06Q 10/06 700/99 |
| 2006/0235557 A1* | 10/2006 | Knight | ................ | G06Q 10/087 700/103 |
| 2008/0015721 A1* | 1/2008 | Spearman | ............. | G06Q 10/06 700/99 |
| 2011/0130857 A1* | 6/2011 | Budiman | ......... | G05B 19/41875 700/104 |
| 2012/0004944 A1* | 1/2012 | Bachman | ......... | G06Q 10/06315 705/7.25 |
| 2018/0137455 A1* | 5/2018 | Mack | ..................... | G06Q 10/04 |

OTHER PUBLICATIONS

Stefan Minner, Multiple-supplier inventory models in supply chainmanagement: A review, International Journal of Production Economics, vols. 81-82, Jan. 11, 2003, pp. 265-279.*

Gerard P. Cachon, Exact Evaluation of Batch-Ordering Inventory Policies in Two-Echelon Supply Chains With Periodic Review, Operations Research, vol. 49, No. 1, Jan.-Feb. 2001, pp. 79-98.*

* cited by examiner

SYSTEM AND METHOD FOR INVENTORY PLANNING IN A SUPPLY CHAIN NETWORK

CROSS-REFERENCE TO RELATED APPLICATIONS

The present disclosure is related to that disclosed in the U.S. Provisional Application No. 62/336,244, filed May 13, 2016, entitled "System and Method for Inventory Planning in a Supply Chain Network." U.S. Provisional Application No. 62/336,244 is assigned to the assignee of the present application. The subject matter disclosed in U.S. Provisional Application No. 62/336,244 is hereby incorporated by reference into the present disclosure as if fully set forth herein. The present invention hereby claims priority under 35 U.S.C. § 119(e) to U.S. Provisional Application No. 62/336,244.

TECHNICAL FIELD

The disclosure relates generally to electronic commerce, and more specifically to a system and method for inventory planning in a supply chain network.

BACKGROUND

Electronic commerce requires the movement of goods throughout a supply chain network with the minimum of human involvement. Retailers frequently stock thousands of items each with different demand, transportation costs, stocking costs, etc. The inability to quickly determine an inventory plan for an electronic commerce system is undesirable.

BRIEF DESCRIPTION OF THE DRAWINGS

A more complete understanding of the present invention may be derived by referring to the detailed description when considered in connection with the following illustrative figures. In the figures, like reference numbers refer to like elements or acts throughout the figures.

DETAILED DESCRIPTION

Aspects and applications of the invention presented herein are described below in the drawings and detailed description of the invention. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Figure 1:
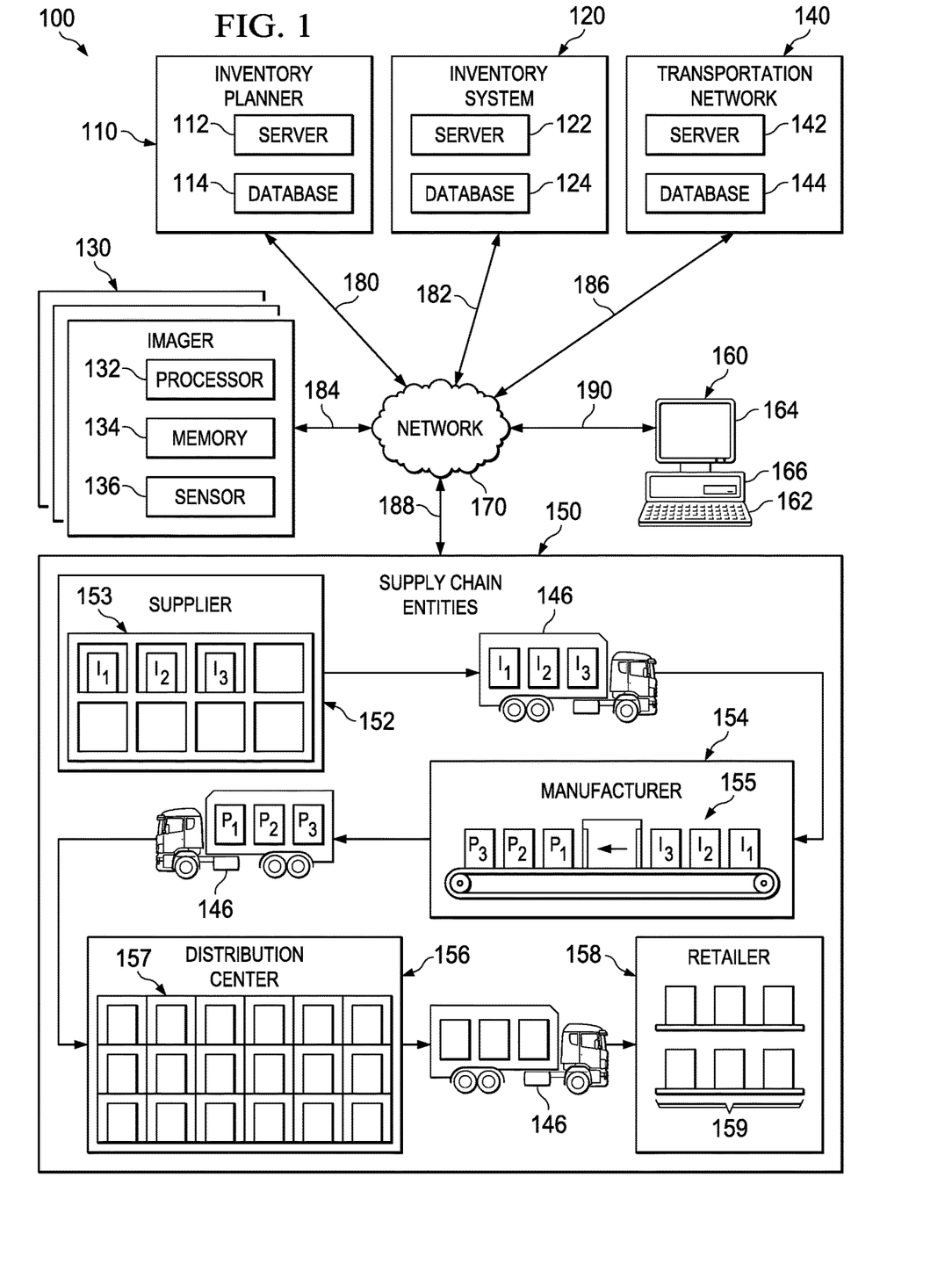
FIG. 1 illustrates an exemplary supply chain network, according to an embodiment.

FIG. 1 illustrates an exemplary supply chain network 100 according to a first embodiment. Supply chain network 100 comprises inventory planner 110, inventory system 120, one or more imagers 130, transportation network 140, one or more supply chain entities 150, computer 160, network 170, and communication links 180-190. Although a single inventory planner 110, a single inventory system 120, a single imager 130, a single transportation network 140, one or more supply chain entities 150, a single computer 160, and a single network 170, are shown and described, embodiments contemplate any number of inventory planners, inventory systems, imagers, transportation systems, supply chain entities, computers, or networks, according to particular needs.

In one embodiment, inventory planner 110 comprises server 112 and database 114. As explained in more detail below, inventory planner 110 determines an inventory policy using a discrete demand distribution (which may also be known as an empirical demand distribution) and a target service level. In addition, or as an alternative, inventory planner 110 may evaluate the determined inventory policy and determine an improved inventory policy using a Markov Chain-based heuristic. The heuristic disclosed herein is much faster than other methods of calculating inventory policies and reduces the computational time and memory usage of the computer. In addition, the heuristic can be used to find inventory policies for a large number of items quickly (such as, for example, over 100,000 items).

According to embodiments, inventory planner 110 evaluates an inventory policy by calculating the cost, no-stockout probability, and fill rate for the inventory policy. The assessment of the quality may be used to measure the quality of a current inventory policy and/or to determine the quality of an inventory policy determined by inventory planner 110, as explained in more detail below. In addition, or as an alternative, inventory planner 110 determines an improved inventory policy based on a local search heuristic.

Inventory system 120 comprises server 122 and database 124. Server 122 of inventory system 120 is configured to receive and transmit item data, including item identifiers, pricing data, attribute data, inventory levels, and other like data about one or more items at one or more locations in the supply chain network 100. Server 122 stores and retrieves item data from database 124 or one or more locations in the supply chain network 100.

One or more imagers 130 comprise an electronic device that receives imaging information from one or more sensors 136 or from one or more databases in supply chain network 100. According to embodiments, one or more imagers 130 comprise one or more processors 132, memory 134, one or more sensors 136, and may include any suitable input device, output device, fixed or removable computer-readable storage media, or the like. According to embodiments, one or more imagers 130 identify items near the one or more sensors 136 and generate a mapping of the item in supply chain network 100. As explained in more detail below, inventory system 120 and transportation network 140 use the mapping of an item to locate the item in the supply chain network 100. The location of the item is then used to coordinate the storage and transportation of items in supply chain network 100 to implement one or more inventory policies generated by inventory planner 110.

One or more imagers 130 may comprise a mobile handheld device such as, for example, a smartphone, a tablet computer, a wireless device, or the like. In addition, or as an alternative, one or more imagers 130 comprise one or more networked electronic devices configured to transmit item identity information to one or more databases as an item passes by or is scanned by imager 130. This may include, for example, a stationary scanner located at one or more supply chain entities 150 that identifies items as the items pass near the scanner. One or more sensors 136 of one or more imagers 130 may comprise an imaging sensor, such as, a camera, scanner, electronic eye, photodiode, charged coupled device (CCD), or any other electronic or manual sensor that detects images of objects. In addition, or as an alternative, one or more sensors 136 may comprise a radio receiver and/or transmitter configured to read an electronic tag, such as, for example, an RFID tag.

Transportation network 140 comprises server 142 and database 144. According to embodiments, transportation network 140 directs one or more transportation vehicles 146 to ship one or more items between one or more supply chain entities 150, based, at least in part, on the quantities of an inventory policy determined by inventory planner 110. Transportation vehicles 146 comprise, for example, any number of trucks, cars, vans, boats, airplanes, unmanned aerial vehicles (UAVs), cranes, robotic machinery, or the like, In addition to the inventory policy, the number of items shipped by transportation vehicles 146 in transportation network 140 may also be based, at least in part, on the number of items currently in stock at one or more supply chain entities 150, the number of items currently in transit in the transportation network 140, forecasted demand, a supply chain disruption, and the like.

As shown in FIG. 1, supply chain network 100 operates on one or more computers 160 that are integral to or separate from the hardware and/or software that support inventory planner 110, inventory system 120, one or more imagers 130, transportation network 140, and one or more supply chain entities 150. Supply chain network 100 comprising inventory planner 110, inventory system 120, one or more imagers 130, transportation network 140, and one or more supply chain entities 150 may operate on one or more computers that are integral to or separate from the hardware and/or software that support the inventory planer 110, inventory system 120, one or more imagers 130, transportation network 140, and one or more supply chain entities 150. Computers 160 may include any suitable input device 162, such as a keypad, mouse, touch screen, microphone, or other device to input information. Output device 164 may convey information associated with the operation of supply chain network 100, including digital or analog data, visual information, or audio information. Computer 160 may include fixed or removable computer-readable storage media, including a non-transitory computer readable medium, magnetic computer disks, flash drives, CD-ROM, in-memory device or other suitable media to receive output from and provide input to supply chain network 100. Computer 160 may include one or more processors 166 and associated memory to execute instructions and manipulate information according to the operation of supply chain network 100 and any of the methods described herein. In addition, or as an alternative, embodiments contemplate executing the instructions on computer 160 that cause computer 160 to perform functions of the method. Further examples may also include articles of manufacture including tangible computer-readable media that have computer-readable instructions encoded thereon, and the instructions may comprise instructions to perform functions of the methods described herein. According to some embodiments, the functions and methods described in connection with imager 130 may be emulated by one or more modules configured to perform the functions and methods as described.

In addition, and as discussed herein, supply chain network 100 may comprise a cloud based computing system having processing and storage devices at one or more locations, local to, or remote from inventory planner 110, inventory system 120, one or more imagers 130, transportation network 140, and one or more supply chain entities 150. In addition, each of the one or more computers 140 may be a work station, personal computer (PC), network computer, notebook computer, tablet, personal digital assistant (PDA), cell phone, telephone, smartphone, wireless data port, augmented or virtual reality headset, or any other suitable computing device. In an embodiment, one or more users may be associated with the inventory planer 110, inventory system 120, one or more imagers 130, transportation network 140, and one or more supply chain entities 150.

These one or more users may include, for example, a "manager" or a "planner" handling determination of inventory policies, managing the inventory of items, imaging items, managing storage and shipment of items, and/or one or more related tasks within supply chain network 100. In addition, or as an alternative, these one or more users within supply chain network 100 may include, for example, one or more computers programmed to autonomously handle, among other things, determining an inventory policy, forecasting demand, controlling manufacturing equipment, and adjusting various levels of manufacturing and inventory levels at various stocking points and distribution centers, and/or one or more related tasks within supply chain network 100.

One or more supply chain entities 150 represent one or more supply chain networks, including one or more enterprises, such as, for example networks of one or more suppliers 152, manufacturers 154, distribution centers 156, retailers 158 (including brick and mortar and online stores), customers, and/or the like. Suppliers 152 may be any suitable entity that offers to sell or otherwise provides one or more items (i.e., materials, components, or products) to one or more manufacturers 154. Suppliers 152 may comprise automated distribution systems 153 that automatically transport products to one or more manufacturers 154 based, at least in part, on an inventory policy determined by inventory planner 110 and/or one or more other factors described herein. In addition, or as an alternative, each of the one or more items may be represented in supply chain network 100 by an identifier, including, for example, Stock-Keeping Unit (SKU), Universal Product Code (UPC), serial number, barcode, tag, RFID, or any other device that encodes identifying information. As discussed above, one or more imagers 130 may generate a mapping of one or more items in the supply chain network 100 by scanning an identifier associated with an item or associated the image of an item with an identifier stored in a database.

Manufacturers 154 may be any suitable entity that manufactures at least one product. Manufacturers 154 may use one or more items during the manufacturing process to produce any manufactured, fabricated, assembled, or otherwise processed item, material, component, good or product. In one embodiment, a product represents an item ready to be supplied to, for example, one or more supply chain entities 150 in supply chain network 100, such retailers 158, an item that needs further processing, or any other item. Manufacturers 154 may, for example, produce and sell a product to suppliers 152, other manufacturers 154, distribution centers 156, retailers 158, a customer, or any other suitable person or entity. Manufacturers 154 may comprise automated robotic production machinery 155 that produce products based, at least in part, on an inventory policy determined by inventory planner 110 and/or one or more other factors described herein.

Distribution centers 156 may be any suitable entity that offers to store or otherwise distribute at least one product to one or more retailers 158 and/or customers. Distribution centers 156 may, for example, receive a product from a first one or more supply chain entities 150 in supply chain network 100 and store and transport the product for a second one or more supply chain entities 150. Distribution centers 156 may comprise automated warehousing systems 157 that automatically remove products from and place products into inventory based, at least in part, on an inventory policy determined by inventory planner 110 and/or one or more other factors described herein.

Retailers 158 may be any suitable entity that obtains one or more products to sell to one or more customers. Retailers 158 may comprise any online or brick and mortar store, including stores with shelving systems 159. Shelving systems may comprise, for example, various racks, fixtures, brackets, notches, grooves, slots, or other attachment devices for fixing shelves in various configurations. These configurations may comprise shelving with adjustable lengths, heights, and other arrangements, which may be adjusted by an employee of retailers 158 based on computer-generated instructions or automatically by machinery to place products in a desired location in retailers 158.

Although one or more supply chain entities 150 are shown and described as separate and distinct entities, the same entity may simultaneously act as any one of the one or more supply chain entities 150. For example, one or more supply chain entities 150 acting as a manufacturer can produce a product, and the same entity can act as a supplier to supply an item to itself or another supply chain entity 150. Although one example of a supply chain network 100 is shown and described, embodiments contemplate any configuration of supply chain network 100, without departing from the scope described herein.

In one embodiment, inventory planner 110 may be coupled with network 170 using communications link 180, which may be any wireline, wireless, or other link suitable to support data communications between inventory planner 110 and network 170 during operation of supply chain network 100. Inventory system 120 may be coupled with network 170 using communications link 182, which may be any wireline, wireless, or other link suitable to support data communications between inventory system 120 and network 170 during operation of supply chain network 100. One or more imagers 130 are coupled with network 170 using communications link 184, which may be any wireline, wireless, or other link suitable to support data communications between one or more imagers 130 and network 170 during operation of distributed supply chain network 100. Transportation network 140 may be coupled with network 170 using communications link 186, which may be any wireline, wireless, or other link suitable to support data communications between transportation network 140 and network 170 during operation of supply chain network 100. One or more supply chain entities 150 may be coupled with network 170 using communications link 188, which may be any wireline, wireless, or other link suitable to support data communications between one or more supply chain entities 150 and network 170 during operation of supply chain network 100. Computer 160 may be coupled with network 170 using communications link 190, which may be any wireline, wireless, or other link suitable to support data communications between computer 160 and network 170 during operation of supply chain network 100.

Although communication links 180-190 are shown as generally coupling one or inventory planner 110, inventory system 120, one or more imagers 130, transportation network 140, one or more supply chain entities 150, and computer 160 to network 170; each of inventory planner 110, inventory system 120, one or more imagers 130, transportation network 140, one or more supply chain entities 150, and computer 160 may communicate directly with each other, according to particular needs.

In another embodiment, network 170 includes the Internet and any appropriate local area networks (LANs), metropolitan area networks (MANs), or wide area networks (WANs) coupling inventory planner 110, inventory system 120, one or more imagers 130, transportation network 140, one or more supply chain entities 150, and computer 160. For example, data may be maintained by locally or externally of inventory planner 110, inventory system 120, one or more imagers 130, transportation network 140, one or more supply chain entities 150, and computer 160 and made available to one or more associated users of inventory planner 110, inventory system 120, one or more imagers 130, transportation network 140, one or more supply chain entities 150, and computer 160 using network 170 or in any other appropriate manner. For example, data may be maintained in a cloud database at one or more locations external to inventory planner 110, inventory system 120, one or more imagers 130, transportation network 140, one or more supply chain entities 150, and computer 160 and made available to one or more associated users of inventory planner 110, inventory system 120, one or more imagers 130, transportation network 140, one or more supply chain entities 150, and computer 160 using the cloud or in any other appropriate manner. Those skilled in the art will recognize that the complete structure and operation of network 170 and other components within supply chain network 100 are not depicted or described. Embodiments may be employed in conjunction with known communications networks and other components.

In accordance with the principles of embodiments described herein, inventory planner 110 may generate an inventory policy for the inventory of one or more supply chain entities 150 in supply chain network 100. Furthermore, inventory planner 110, inventory system 120, and/or transportation network 140 may instruct automated machinery (i.e., robotic warehouse systems, robotic inventory systems, automated guided vehicles, mobile racking units, automated robotic production machinery, robotic devices and the like) to adjust product mix ratios, inventory levels at various stocking points, production of products of manufacturing equipment, proportional or alternative sourcing of one or more supply chain entities 150, and the configuration and quantity of packaging and shipping of products based on one or more generated plans and policies and/or current inventory or production levels. For example, according to embodiments, inventory planner 110 determines an inventory policy based on an item demand distribution and a target service level. The determined inventory policy may comprise an (s, S) inventory policy, which signifies that when the inventory quantity of an item reaches a quantity s (reorder point) or less, the item may be resupplied to reach a quantity S (target quantity). Therefore, when the inventory of an item falls to the reorder point, inventory planner 110 may then automatically adjust product mix ratios, inventory levels, production of products of manufacturing equipment, and proportional or alternative sourcing of one or more supply chain entities until the inventory is resupplied to the target quantity.

For example, the methods described herein may include computers receiving product data from automated machinery having at least one sensor and the product data corresponding to an item detected by the automated machinery. The received product data may include an image of the item, an identifier, as described above, and/or other product data associated with the item (dimensions, texture, estimated weight, and any other like data). The method may further include computers looking up the received product data in a database system associated with inventory planner 110, inventory system 120, and/or transportation network 140 to identify the item corresponding to the product data received from the automated machinery.

The computers may also receive, from the automated machinery, a current location of the identified item. Based on the identification of the item, computers may also identify (or alternatively generate) a first mapping in the database system, where the first mapping is associated with the current location of the item. Computers may also identify a second mapping in the database system, where the second mapping is associated with a past location of the identified item. Computers may also compare the first mapping and the second mapping to determine if the current location of the identified item in the first mapping is different than the past location of the identified item in the second mapping. Computers may then send instructions to the automated machinery based, as least in part, on one or more differences between the first mapping and the second mapping such as, for example, to locate item to add to or remove from an inventory of or shipment for one or more supply chain entities 150. In addition, or as an alternative, digital hub 110 monitors the supply chain constraints of one or more items at one or more supply chain entities 150 and adjusts the orders and/or inventory of the one or more supply chain entities 150 based on the supply chain constraints.

Figure 2:
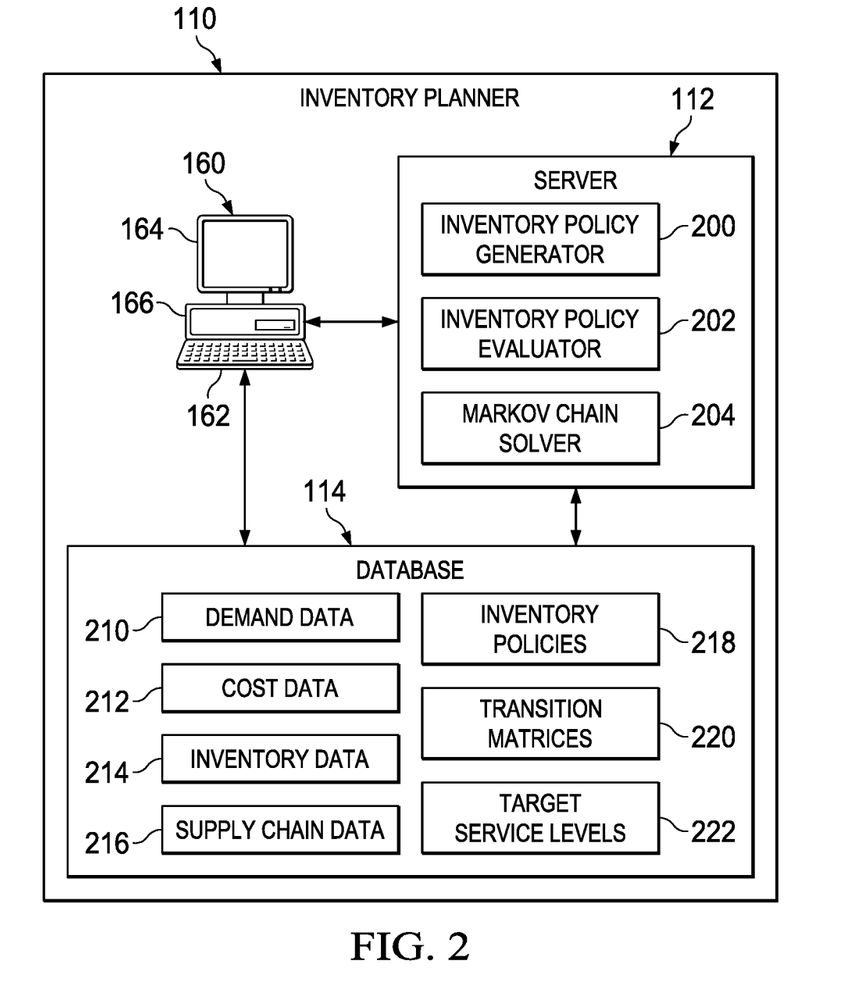
FIG. 2 illustrates the inventory planner of FIG. 1, according to an embodiment.

FIG. 2 illustrates inventory planner 110 of FIG. 1 in greater detail in accordance with an embodiment. As discussed above, inventory planner 110 may comprise one or more computers 160 at one or more locations including associated input devices 162, output devices 164, non-transitory computer-readable storage media, processors 166, memory, or other components for receiving, processing, storing, and communicating information according to the operation of supply chain network 100. Additionally, inventory planner 110 comprises server 112 and database 114. Although inventory planner 110 is shown as comprising a single computer 160, a single server 112 and a single database 114; embodiments contemplate any suitable number of computers, servers, or databases internal to or externally coupled with inventory planner 110. According to some embodiments, inventory planner 110 may be located internal to one or more retailers 158 of one or more supply chain entities 150. In other embodiments, inventory planner 110 may be located external to one or more retailers 158 of one or more supply chain entities 150 and may be located in for example, a corporate retailer of the one or more retailers 158, according to particular needs.

Server 112 of inventory planner 110 may comprise inventory policy generator 200, inventory policy evaluator 202, and Markov Chain solver 204. Although server 112 is shown and described as comprising a single inventory policy generator 200, a single inventory policy evaluator 202, and a single Markov Chain solver 204, embodiments contemplate any suitable number or combination of these located at one or more locations, local to, or remote from inventory planner 110, such as on multiple servers or computers at any location in supply chain network 100.

Database 114 of inventory planner 110 may comprise one or more databases or other data storage arrangement at one or more locations, local to, or remote from, server 112. Database 114 comprises, for example, demand data 210, cost data 212, inventory data 214, supply chain data 216, inventory policies 218, transition matrices 220, and target service levels 222. Although, database 114 is shown and described as comprising demand data 210, cost data 212, inventory data 214, supply chain data 216, inventory policies 218, transition matrices 220, and target service levels 222, embodiments contemplate any suitable number or combination of these, located at one or more locations, local to, or remote from, inventory planner 110 according to particular needs.

In one embodiment, inventory policy generator 200 of inventory planner 110 uses a policy heuristic to generate an inventory policy based on a discrete demand distribution and a target service level. For example, inventory policy generator 200 may receive a discrete demand distribution comprising a probability associated with each demand quantity for a particular item and a target service level comprising a percentile to which the safety stock is set. According to some embodiments, inventory policy generator 200 determines a discrete demand distribution and/or a target service level based on supply chain data 216 received from one or more supply chain entities 150. Supply chain data 216 may comprise any data of the one or more supply chain entities 150 including, for example, item data, identifiers, metadata (comprising dimensions, hierarchies, levels, members, attributes, and member attribute values), fact data (comprising measure values for combinations of members), and various decision variables, business constraints, goals and objectives of one or more supply chain entities 150.

Once inventory policy generator 200 receives or determines the discrete demand distribution and/or a target service level, it may then determine the inventory policy. According to some embodiments, the inventory policy determined by inventory policy generator 200 comprises an (s, S) inventory policy, which represents a reorder point, s, and a target quantity, S. Inventory policy generator 200 calculates an inventory policy differently depending on whether the item is a slow-mover item or a fast-mover item. The choice of the type of the item (slow-mover or fast-mover) may be assigned by the user or automatically by inventory policy generator 200 based on predetermined criteria such as, for example, a threshold on the expected demand over a leadtime duration. By way of example only and not by way of limitation, if the average demand of an item is below a particular threshold, such as, for example, 20 units or any other suitable level, for the time it takes for an order to arrive, it may be classified as a slow-mover. If not, it may be classified as a fast-mover.

After the reorder point and target quantity is calculated for each item, an initial inventory policy is set for the items and may be stored as inventory policies 218 in database 114 of inventory planner 110. After the inventory policies are determined, the inventory policies may be evaluated by inventory policy evaluator 202.

In one embodiment, inventory policy evaluator 202 uses a Markov chain-based heuristic to determine the quality of one or more inventory policies, which may include the inventory policy determined by inventory policy generator 200. For example, inventory policy evaluator 202 may measure the quality of an inventory policy using a Markov chain model to obtain one or more measures of quality for an inventory policy, including: a no-stockout probability, a fill rate, and/or a cost. According to some embodiments, inventory policy evaluator 202 determines an improved inventory policy based on a local search heuristic. According to an embodiment, to calculate the inventory policy quality, inventory policy evaluator 202 determines a transition matrix based on a Markov chain, which gives the probability of being in one or more inventory states. The determined transition matrix may comprise a set of states of different inventory levels and the probability of transitioning between each pair of states. The transition matrix depends on the particular demand distribution and inventory policy that is evaluated. Once the transition matrix is determined, Markov chain solver 204 of inventory planner 110 may solve the transition matrix to determine a solution vector, comprising the probability of being in a state at any time. Markov chain solver 204 of inventory planner 110 may comprise any suitable solver that receives the transition matrix from inventory policy evaluator 202 and determines a solution probability vector comprising the probability of being in a state at any time. Inventory policy generator 200, inventory policy evaluator 202, and Markov chain solver 204 will be discussed in more detail in connection with the method of FIG. 3 below.

The various types of data stored in the database of inventory planner will now be discussed.

In one embodiment, demand data 210 of database 114 may comprise for example, any data relating to past sales, past demand, purchase data, promotions, events, or the like of one or more supply chain entities 150. Demand data 210 may be stored at time intervals such as, for example, by the minute, hour, daily, weekly, monthly, quarterly, yearly, or any suitable time interval, including substantially in real time. According to embodiments, demand data 210 includes a demand function, comprising demand values and probabilities. For a historical demand, a demand function may comprise probabilities calculated from a frequency associated with demand value for one or more time steps. According to embodiments, demand data 210 may be used to determine a discrete demand distribution and/or a target service level.

Cost data 212 of database 114 may comprise any one or more general cost components of one or more items in the supply chain network 100, such as, for example, holding costs, batch costs, stockout costs, inventory costs, order costs, backorder costs, and backlog costs. According to some embodiments, inventory policy evaluator 202 uses cost data 212 to calculate a cost associated with an inventory policy.

Inventory data 214 of database 114 may comprise any data relating to current or projected inventory quantities or states, order rules, or explanatory variables. For example, inventory data 214 may comprise the current level of inventory for each item at one or more stocking points across the supply chain network 100. In addition, inventory data 214 may comprise order rules that describe one or more rules or limits on setting an inventory policy, including, but not limited to, a minimum order quantity, a maximum order quantity, a discount, and a step-size order quantity, and batch quantity rules. According to some embodiments, inventory data 214 may comprise explanatory variables that describe the data relating to specific past, current, or future indicators and the data of promotions, seasonality, special events (such as sporting events), weather, and the like. According to some embodiments, inventory planner 110 accesses and stores inventory data 214 in database 114, which may be used by inventory planner 110 to place orders, set inventory levels at one or more stocking points, initiate manufacturing of one or more components, or the like. In addition, or as an alternative, inventory data 214 may be updated by receiving current item quantities, mappings, or locations from inventory system 120, one or more imagers 130, and/or transportation system 140.

Inventory policies 218 of database 114 may comprise any suitable inventory policy describing the reorder point and target quantity, or other inventory policy parameters that set rules for inventory planner 110 to manage and reorder inventory. Such inventory policies may be based on target service level, demand data 210, cost data 212, fill rate, or other like inputs that provide for determining inventory policies. According to embodiments, inventory policies 218 may be determined by inventory policy generator 200 based on a demand distribution and a target service level. According to embodiments, inventory policies 218 may be used by inventory policy evaluator 202 to determine a no-stockout probability, fill rate, cost, or other like determination of an inventory policy. According to some embodiments, inventory policies 218 may be used by inventory policy evaluator 202 to determine an improved inventory policy based on a local search heuristic.

In one embodiment, inventory policy evaluator 202 may generate transition matrices 220 comprising one or more mathematical matrices or data structures that comprise data determined by inventory policy evaluator 202 that defines the probability of moving from each possible inventory state to another during a period. According to embodiments, transition matrices 220 may be used by inventory policy evaluator 202 to determine solution vector comprising a probability of being in any particular inventory state at any particular time. The solution vector may then be used by inventory policy evaluator 202 to determine no-stockout probability, fill rate, or cost of the inventory policy and/or determine an improved inventory policy based on a local search heuristic.

Target service level data 142 of database 114 may be calculated by inventory planner 110 from a forecasted demand to ensure that a service level of one or more supply chain entities 150 is met with a certain probability. Target service level data 142 may comprise any suitable service level target. According to some embodiments, one or more supply chain entities 150 set a service level at 95%, meaning the one or more supply chain entities 150 will set the desired inventory stock level at a level that meets demand 95% of the time. Although, a particular service level target and percentage is described; embodiments contemplate any service target or level, for example, a service level of approximately 99% through 90%, a 75% service level, or any suitable service level, according to particular needs. Other types of service levels associated with inventory quantity or order quantity may comprise, but are not limited to, a maximum expected backlog and a fulfillment level. Once the service level is set, inventory planner 110 may determine a replenishment order according to one or more replenishment rules, which, among other things, indicates to one or more supply chain entities 150 to determine or receive inventory to replace the depleted inventory.

Figure 3:
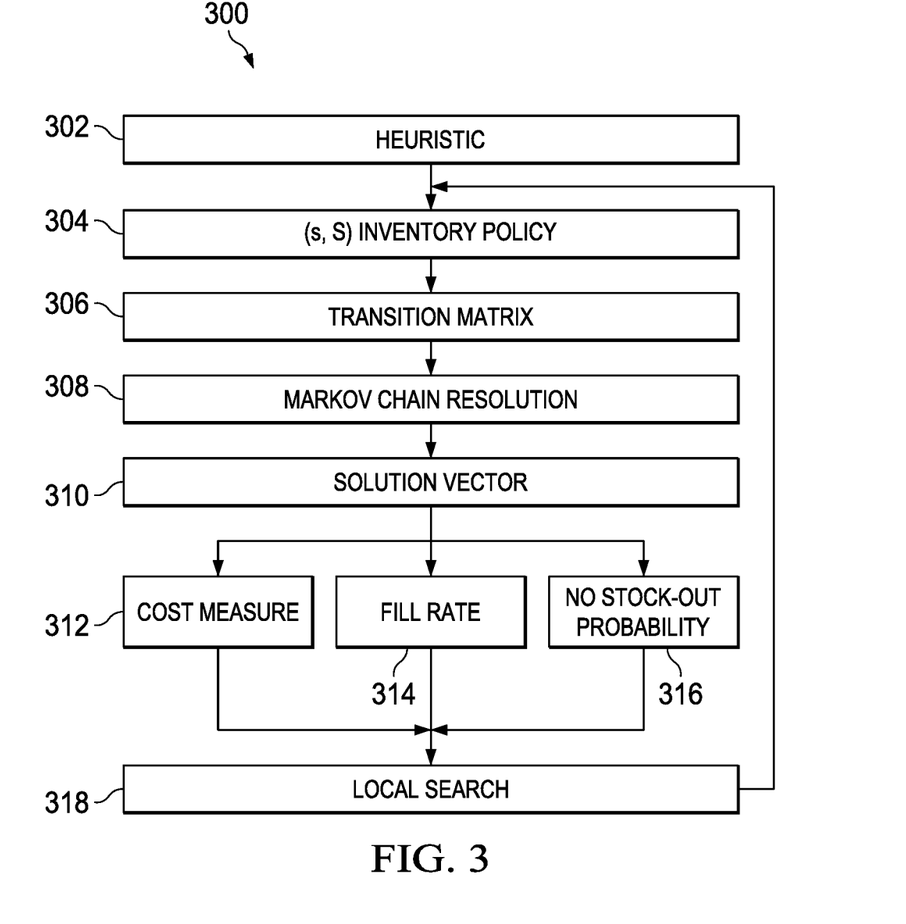
FIG. 3 illustrates a method of determining, evaluating, and improving an inventory policy, according to an embodiment.

FIG. 3 illustrates an exemplary method 300 of determining, evaluating, and improving an inventory policy by inventory planner 110 according to an embodiment. The following method 300 proceeds by one or more activities, which although described in a particular order may be performed in one or more permutations, according to particular needs. Method 300 begins at activity 302 where inventory planner 110 initiates a heuristic to determine an inventory policy. At activity 304, inventory policy generator 200 of inventory planner 110 generates or receives an inventory policy based on a demand distribution and a target service level for each of one or more items.

As discussed above, inventory policy generator 200 of inventory planner 110 uses an inventory policy heuristic to determine an inventory policy based on a discrete demand distribution and a target service level. For example, inventory policy generator 200 may receive a discrete demand distribution comprising a probability associated with each inventory state for a particular item and a target service level comprising a percentile to which the safety stock is set. According to some embodiments, inventory policy generator 200 determines a discrete demand distribution and/or a target service level based on the supply chain data received from one or more supply chain entities 150, as described above.

Figure 4:
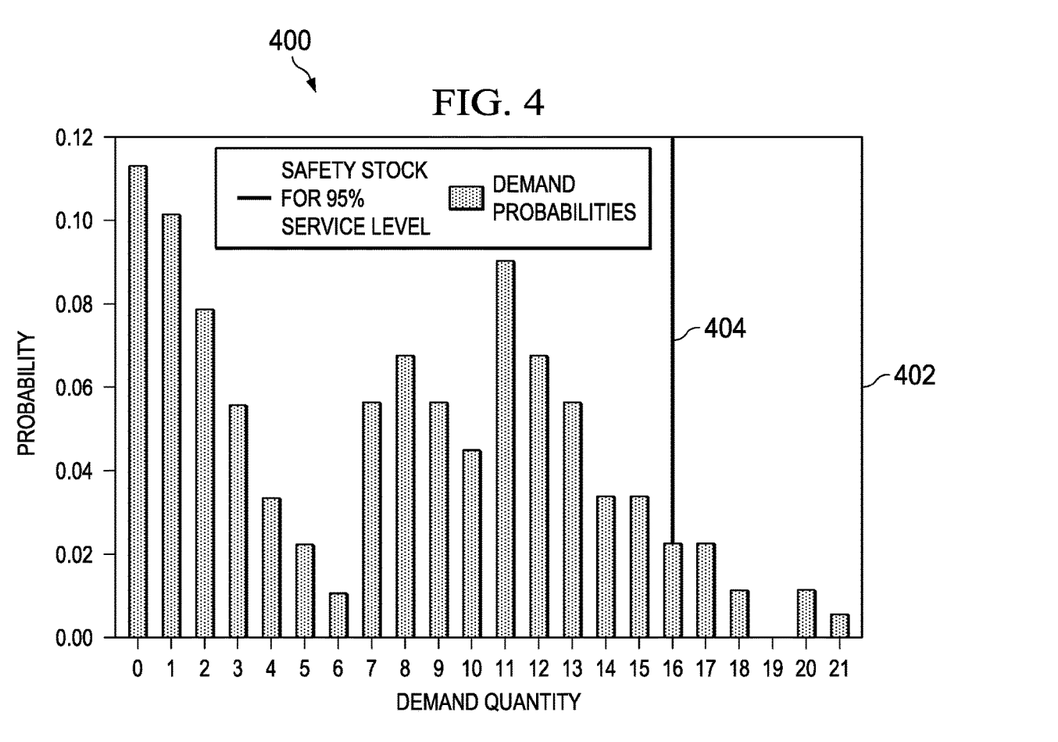
FIG. 4 illustrates a graph of a discrete demand distribution and a target service level, according to an embodiment.

FIG. 4 illustrates a graph 400 of a discrete demand distribution and a target service level. A discrete demand distribution 402 associates each quantity of an item demand with a probability of that demand occurring over a particular time frame (i.e. the demand quantity for each day, week, month, or any suitable time period). In the illustrated demand distribution, the probability of a demand of seven units has approximately a 6% chance of occurring. A demand of eleven units has approximately a 9% chance of occurring. The target service level 404 is also illustrated. The target service level 404 is represented as a vertical line indicating the percentile for which a safety stock is set. As illustrated, a safety stock for 95% satisfaction of demands would require a safety stock of approximately sixteen units.

Once inventory policy generator 200 receives or determines the discrete demand distribution and/or a target service level, it may then determine the inventory policy. According to some embodiments, the inventory policy comprises an (s, S) inventory policy, which represents a reorder point, s, and a target quantity, S. Inventory policy generator 200 calculates an inventory policy differently depending on whether the item is a slow-mover or a fast-mover. For both a slow-mover and a fast-mover, the reorder point, s, is set as the demand quantity of the discrete demand distribution 402 that has the same percentile as the target service level 404. For the illustrated demand distribution 402, the reorder point would be sixteen units, which corresponds to a 95% service level.

As discussed above, to calculate the target quantity, S, a slow-mover and a fast-mover are calculated differently. If the item is a fast-mover, the target quantity is obtained by adding the reorder point to an Economic Order Quantity (EOQ). In other words, S=s+EOQ. The EOQ may be calculated by:

$$EOQ = \sqrt{\frac{2K\lambda}{IC}} \quad (1)$$

where K is a fixed order cost, $\lambda$ is a total expected yearly demand, I is an inventory cost, and C is a unit cost. For the example just given, if the EOQ was calculated as, hypothetically, seven units, then the target quantity would equal twenty-three units (16+7=23).

If the item is a slow-mover, the target quantity is obtained by adding the reorder point to 1. In other words, S=s+1.

After the reorder point and target quantity is calculated for each item, an initial inventory policy is set for the items and may be stored as inventory policies 218 in database 114 of inventory planner 110. After the inventory policies are determined, the method may proceed to activity 306. At activity 306, inventory policy evaluator 202 determines a transition matrix to assess the quality of one or more inventory policies. For example, inventory policy evaluator 202 may measure the quality of an inventory policy using a solution vector to obtain one or more measures of quality for an inventory policy, including a no-stockout probability, a fill rate, and/or a cost.

In one embodiment, the determined transition matrix may comprise a set of states of different inventory levels and the probability of transitioning between each pair of states. The transition matrix may depend on the particular demand distribution and the inventory policy that is evaluated. The transition matrix may be determined from an (s, S) inventory policy, which is not based on a fixed order quantity. According to embodiments, the discrete demand probability may be received by one or more supply chain entities 150 or calculated by inventory policy generator 200 based on, for example, historical sales or other demand data.

By way of example only and not by way of limitation, an example is now given. In the following example, the states of the transition matrix are the possible inventory on-hand levels at each period. The demands that cannot be satisfied during a period are represented by negative inventory quantities.

Let $P=[-b, \ldots, 0, \ldots, u+1]$ be the set of inventory states where b is the minimum inventory which can be capped by the maximum demand and u is the maximum inventory quantity. The state u+1 is the absorbing state. This special state may have a very high penalty that provides for limiting the size of the inventory. A transition matrix associated with an order quantity can be constructed in the following manner. The probability of staying in a state, s, is equal to the probability of not having any demand. The probability of moving from state s to state s−d is equal to the probability of having a demand of d items during a single time step. Moving from state $s_1$ to state $s_2$ where $s_1 < s_2$ is impossible if no order is made.

Let i be a state of the inventory (i.e. the inventory on-hand level). If the inventory is in a backlogged state (such that i<0), an order of |i| is made. This forces the inventory to exit the backlogged states at each period. An example of a discrete demand probability is shown in matrix (2), below, which represents: during a time step, there is a probability of 63% to have no demand, and a probability of 7%, 22%, 5%, and 3% to have a demand of 1, 2, 3, and 4, respectively.

For example, if the inventory was currently at zero, inventory planner would order three based on an (s, S) inventory policy of (1, 3) because the current inventory level (0) is less than the reorder point (1). Inventory planner 110 would order 3 units of the item, because the current inventory level is 0 and the target quantity is 3 (3−0=3). Based on the demand probability, inventory planner 110 would determine that the probability of staying at an inventory level of 3 is 63%, because the probability is 63% that there will be zero demand. If, on the other hand, the current inventory level is 2, then inventory planner 110 would not reorder because the current inventory level (2) is not less than or equal to the reorder point (1). Inventory planner 110 would determine that the probability of staying at an inventory level of 2 is 63% because the probability is 63% that there will be no demand. The probability of the inventory level decreasing to inventory levels of 1, 0, −1, and −2 would be 7%, 22%, 5%, and 3%, respectively.

Considering an (s, S) inventory policy of (1, 3) and the following discrete demand distribution indicated in (2), inventory policy evaluator 202 determines the transition matrix indicated in (3).

$$\begin{matrix} 0 & 1 & 2 & 3 & 4 \\ [0.63 & 0.07 & 0.22 & 0.05 & 0.03] \end{matrix} \quad (2)$$

$$P_{(1,3)} = \begin{bmatrix} & -2, & -1, & 0, & 1, & 2, & 3, \\ -2 & 0 & 0.03 & 0.05 & 0.22 & 0.07 & 0.63 \\ -1 & 0 & 0.03 & 0.05 & 0.22 & 0.07 & 0.63 \\ 0 & 0 & 0.03 & 0.05 & 0.22 & 0.07 & 0.63 \\ 1 & 0 & 0.03 & 0.05 & 0.22 & 0.07 & 0.63 \\ 2 & 0.03 & 0.05 & 0.22 & 0.07 & 0.63 & 0 \\ 3 & 0 & 0.03 & 0.05 & 0.22 & 0.07 & 0.63 \end{bmatrix} \quad (3)$$

Once the transition matrix is determined, method 300 proceeds to activity 308, where Markov chain solver 204 of inventory planner 110 may solve the transition matrix to determine a solution vector, comprising the probability of being in a state at any time.

Markov chain solver 204 of inventory planner 110 may comprise any suitable solver that receives the transition matrix from inventory policy evaluator 202 and determines a solution probability vector comprising the probability of being in a state at any time.

Once the transition matrix (3) is determined, Markov chain solver 204 may solve the transition matrix and method 300 proceeds to activity 310.

At activity 310, Markov chain solver 204 determines a solution vector, v=vP. The vector v contains the probability of being in a state at any time. For example, based on transition matrix (3), the resulting solution vector is equal to solution vector (4).

$$\begin{matrix} -2 & -1 & 0 & 1 & 2 & 3 \\ [0.0048 & 0.0331 & 0.0769 & 0.1963 & 0.1586 & 0.5303] \end{matrix} \quad (4)$$

Once the solution vector is determined, method 300 proceeds to one or more of activities 312, 314, and 316 where inventory policy evaluator 202 evaluates the quality of the inventory policy from which the transition matrix was determined.

At activity 312, inventory policy evaluator 202 first calculates a cost associated with each possible inventory state. A weighted sum (where the weight is the values of the Markov chain solution) gives the expected cost. Costs such as holding costs, order costs, and backorder costs may be taken into account.

To further illustrate, an example is now given. Continuing with the above example, let h=3 be the cost of holding a quantity of one unit of the item in an inventory; let r=8 be the order cost for one item; and let b=20 be the backorder cost (which may also be known as a stockout cost). Based on the (s, S) policy of (1, 3), the resulting cost vector is vector (5).

$$\begin{matrix} -2 & -1 & 0 & 1 & 2 & 3 \\ [28 & 28 & 8 & 11 & 6 & 9] \end{matrix} \quad (5)$$

Inventory policy evaluator 202 then calculates a scalar product between the cost vector (vector (5)) and the Markov chain solution (solution vector (4)) which determines the expected cost per time period for the inventory policy. In this example, the inventory policy cost is equal to 9.56.

At activity 314, inventory policy evaluator calculates a fill rate by first calculating the expected backlog. The backlog may be calculated by computing a weighted sum on the negative states: the probability of being in each negative state may be multiplied by the inventory quantity. For example, let b be the expected backlog and μ be the average demand. The fill rate is therefore equal to $$1 - \frac{b}{\mu}.$$

To further illustrate, an example is now given. Using the solution vector (4), the expected backlog may be calculated as b=2·0.0048+1·0.0331=0.0427. Using demand distribution (2), the average demand may be calculated as μ=1·0.07+2·0.22+3·0.05+4·0.03=0.78. Therefore, the fill rate would be equal to 94.53%

$$\left(\text{i.e. } 1 - \frac{0.427}{0.78} = 0.9453\right).$$

At activity 316, inventory policy evaluator 202 calculates the proportion of the time that an inventory is not in a stockout state. Inventory policy evaluator 202 may then determine the no-stockout probability by summing the probabilities of the states corresponding to inventory levels greater than or equal to 0. To further illustrate, an example is now given. For the solution vector (4), the no-stockout probability is 96.21%, which is calculated according to: (7.69%+19.63%+15.86%+53.03%).

After one or more of activities 312-316, method 300 continues to activity 318 where inventory policy evaluator 202 may use a local search heuristic to determine an improved inventory policy from any inventory policy. The local search heuristic may improve an inventory policy by iterating through a series of activities to determine potentially improved inventory polices and evaluating the cost, fill rate, and/or no stock-out probability of the potentially improved inventory policies (provisional inventory policies).

The local search activity begins by choosing an integer step size, k, which may be any integer, such as 1, 2, 3, or any other suitable integer. Although the integer step size may be chosen as 1, for large inventories, the integer step size may be larger to increase the speed and/or efficiency of the local search heuristic. After the integer step size, k, is chosen, the local search heuristic determines one or more provisional inventory polices, according to the following:

Increasing the reorder point, s, by integer step size, k, i.e. evaluate the provisional inventory policy (s+k, S);
Reducing the reorder point, s, by integer step size, k, i.e. evaluate the provisional inventory policy (s−k, S);

Reducing the target quantity, S, by integer step size, k, i.e. evaluate the provisional inventory policy (s, S−k); and Increasing the target quantity, S, by integer step size, k, i.e. evaluate the provisional inventory policy (s, S+k).

For each of the provisional inventory policies, inventory policy evaluator 202 returns to activity 304 activity of the method, and uses the provisional inventory policies as input. Inventory policy evaluator 202 determines a transition matrix and solution vector for each of the provisional inventory policies, and evaluates the quality of the provisional inventory polices for cost, fill rate, and/or no-stockout probability, as described above.

For each provisional inventory policy, inventory policy evaluator 202 checks if the provisional inventory policy is better than the initial inventory policy. In this process, the evaluator will first check if all constraints are met, and any inventory policies where constraints are violated will be disregarded. A best inventory policy may then be chosen among the remaining policies by comparing the objective function (such as, for example, a total operating cost), which may be predetermined by the user.

After each of the provisional inventory policies are compared with the initial inventory policy, any improved policy may be reevaluated according to the local search heuristic. That is, any improved provisional inventory policy will be set as the initial inventory policy and the local search activity will be repeated for four new provisional inventory policies as explained above. Each of the four new provisional inventory policies will be evaluated by cost, fill rate, and/or no-stockout probability, and these will be compared to the improved provisional inventory policy, and any improved policy will be again evaluated until no further improved inventory policies are found. At this point, method 300 may end.

The above method 300 relates to determining an (s, S) inventory policy from a heuristic but does not rely on a Markov Decision Process (MDP), which makes this method much faster. Additionally, the above method does not use an MDP to force an obtained (s, S) inventory policy to respect a target service level, but instead may compute the service level based on an existing (s, S) inventory policy.

Reference in the foregoing specification to "one embodiment", "an embodiment", or "some embodiments" means that a particular feature, structure, or characteristic described in connection with the embodiment is included in at least one embodiment of the invention. The appearances of the phrase "in one embodiment" in various places in the specification are not necessarily all referring to the same embodiment.

While the exemplary embodiments have been shown and described, it will be understood that various changes and modifications to the foregoing embodiments may become apparent to those skilled in the art without departing from the spirit and scope of the present invention.

What is claimed is:

1. A computer-implemented method for searching alternate inventory policies from an initial inventory policy of an inventory of one or more supply chain entities to a target inventory policy by a computer, comprising:

receiving a current state of items in a supply chain network comprising one or more supply chain entities, wherein an inventory of the one or more supply chain entities is used to store one or more items, and a state of the items comprises a quantity and ordered flow among the inventory of the one or more supply chain entities;

determining an initial inventory policy comprising a reorder point and a target quantity, wherein the initial inventory policy of the inventory is based, at least in part, on a target service level and a discrete demand distribution that is indicative of the projected demand for an item in the inventory for one or more successive periods;

identifying one or more provisional inventory policies to set a provisional reorder point and a provisional target quantity for the one or more items by using a local search heuristic;

calculating one or more of a cost, a fill rate, and a no-stockout probability of the one or more provisional inventory policies based, at least in part, on one or more solution vectors comprising probabilities of the one or more items being in a particular inventory state at a particular time, the solution vector based, at least in part, on one or more transition matrices defining probabilities of moving between one or more possible inventory states;

in response to calculating the one or more cost, fill rate, and no-stockout probability of the one or more provisional inventory policies, selecting a provisional inventory policy that minimizes the cost and no-stockout probability and maximizes the fill rate; and based on the selected provisional inventory policy, causing items to be transported among the one or more supply chain entities to restock the inventory of the one or more items according to the current state of items in the supply chain network.

2. The computer-implemented method of claim 1, further comprising:

evaluating the performance of the initial inventory policy based, at least in part, on a discrete demand distribution of at least one of the one or more items using a Markov chain.

3. The computer-implemented method of claim 2, further comprising:

increasing the reorder point, s, by an integer step size, k, and evaluating as to cost, fill rate, and no-stockout probability a provisional inventory policy comprising (s+k, S);

reducing the reorder point, s, by integer step size, k, and evaluating as to cost, fill rate, and no-stockout probability a provisional inventory policy comprising (s−k, S);

increasing the target quantity, S, by integer step size, k, and evaluating as to cost, fill rate, and no-stockout probability a provisional inventory policy comprising (s, S+k); and reducing the target quantity, S, by integer step size, k, and evaluating as to cost, fill rate, and no-stockout probability a provisional inventory policy comprising (s, S−k).

4. The computer-implemented method of claim 3, wherein the selected provisional inventory policy is the target inventory policy.

5. The computer-implemented method of claim 4, wherein calculating the fill rate of the one or more provisional inventory policies comprises calculating the expected backlog from a weighted sum of negative inventory states, wherein the probability of being in each negative state is multiplied by an inventory quantity.

6. The computer-implemented method of claim 5, wherein the inventory policy comprises an (s, S) inventory policy.

7. The computer-implemented method of claim 6, wherein calculating the no-stockout probability comprises summing probabilities of the state of the items corresponding to inventory levels greater than or equal to zero.

8. An automatic inventory restocking system, comprising:
a server, comprising one or more processors and memory, configured to:
receive a current state of items in a supply chain network comprising one or more supply chain entities;
determine an initial inventory policy comprising a reorder point and a target quantity, wherein the initial inventory policy of an inventory is based, at least in part, on a target service level and a discrete demand distribution that is indicative of a projected demand for an item in the inventory for one or more successive periods;
identify one or more provisional inventory policies to set a provisional reorder point and a provisional target quantity for the one or more items by using a local search heuristic;
calculate one or more of a cost, a fill rate, and a no-stockout probability of the one or more provisional inventory policies based, at least in part, on one or more solution vectors comprising probabilities of the one or more items being in a particular inventory state at a particular time, the solution vector based, at least in part, on one or more transition matrices defining probabilities of moving between one or more possible inventory states; and
in response to calculating the one or more cost, fill rate, and no-stockout probability of the one or more provisional inventory policies, select a provisional inventory policy that minimizes the cost and no-stockout probability and maximizes the fill rate, wherein causing at least one of one or more transportation vehicles to transport items among the one or more supply chain entities to restock the inventory of the one or more items according to the current state of items in the supply chain network based on the selected provisional inventory policy.

9. The automatic inventory restocking system of claim 8, wherein the server is further configured to:
evaluate the performance of the initial inventory policy based, at least in part, on a discrete demand distribution of at least one of the one or more items using a Markov chain.

10. The automatic inventory restocking system of 9, wherein the server is further configured to:
increase the reorder point, s, by an integer step size, k, and evaluate as to cost, fill rate, and no-stockout probability a provisional inventory policy comprising (s+k, S);
reduce the reorder point, s, by integer step size, k, and evaluate as to cost, fill rate, and no-stockout probability a provisional inventory policy comprising (s−k, S);
increase the target quantity, S, by integer step size, k, and evaluate as to cost, fill rate, and no-stockout probability a provisional inventory policy comprising (s, S+k); and
reduce the target quantity, S, by integer step size, k, and evaluate as to cost, fill rate, and no-stockout probability a provisional inventory policy comprising (s, S−k).

11. The automatic inventory restocking system of claim 10, wherein the selected provisional inventory policy is the target inventory policy.

12. The automatic inventory restocking system of claim 11, wherein the server calculates the fill rate of the one or more provisional inventory policies by calculating the expected backlog from a weighted sum of negative inventory states, wherein the probability of being in each negative state is multiplied by an inventory quantity.

13. The automatic inventory restocking system of claim 12, wherein the inventory policy comprises an (s, S) inventory policy.

14. The automatic inventory restocking system of claim 13, wherein the server calculates the no-stockout probability by summing probabilities of the state of the items corresponding to inventory levels greater than or equal to zero.

15. A non-transitory computer-readable medium embodied with software, the software when executed configured to search alternate inventory policies from an initial inventory policy of an inventory of one or more supply chain entities to a target inventory policy by:
receiving a current state of items in a supply chain network comprising one or more supply chain entities, wherein an inventory of the one or more supply chain entities is used to store one or more items, and a state of the items comprises a quantity and ordered flow among the inventory of the one or more supply chain entities;
determining an initial inventory policy comprising a reorder point and a target quantity, wherein the initial inventory policy of the inventory is based, at least in part, on a target service level and a discrete demand distribution that is indicative of the projected demand for an item in the inventory for one or more successive periods;
identifying one or more provisional inventory policies to set a provisional reorder point and a provisional target quantity for the one or more items by using a local search heuristic;
calculating one or more of a cost, a fill rate, and a no-stockout probability of the one or more provisional inventory policies based, at least in part, on one or more solution vectors comprising probabilities of the one or more items being in a particular inventory state at a particular time, the solution vector based, at least in part, on one or more transition matrices defining probabilities of moving between one or more possible inventory states;
in response to calculating the one or more cost, fill rate, and no-stockout probability of the one or more provisional inventory policies, selecting a provisional inventory policy that minimizes the cost and no-stockout probability and maximizes the fill rate; and
based on the selected provisional inventory policy, using items to be transported among the one or more supply chain entities to restock the inventory of the one or more items according to the current state of items in the supply chain network.

16. The non-transitory computer-readable medium of claim 15, the software when executed further configured to:
evaluate the performance of the initial inventory policy based, at least in part, on a discrete demand distribution of at least one of the one or more items using a Markov chain.

17. The non-transitory computer-readable medium of claim 16, the software when executed further configured to:
increase the reorder point, s, by an integer step size, k, and evaluate as to cost, fill rate, and no-stockout probability a provisional inventory policy comprising (s+k, S);
reduce the reorder point, s, by integer step size, k, and evaluate as to cost, fill rate, and no-stockout probability a provisional inventory policy comprising (s−k, S);

increase the target quantity, S, by integer step size, k, and evaluate as to cost, fill rate, and no-stockout probability a provisional inventory policy comprising (s, S+k); and reduce the target quantity, S, by integer step size, k, and evaluate as to cost, fill rate, and no-stockout probability a provisional inventory policy comprising (s, S−k).

18. The non-transitory computer-readable medium of claim 17, wherein calculating the fill rate of the one or more provisional inventory policies comprises calculating the expected backlog from a weighted sum of negative inventory states, wherein the probability of being in each negative state is multiplied by an inventory quantity.

19. The non-transitory computer-readable medium of claim 18, wherein the selected provisional inventory policy is the target inventory policy.

20. The non-transitory computer-readable medium of claim 19, wherein calculating the no-stockout probability comprises summing probabilities of the state of the items corresponding to inventory levels greater than or equal to zero.

* * * * *